(12) United States Patent       (10) Patent No.:    US 8,168,182 B2
Epshtein                                                    (45) Date of Patent:      May 1, 2012

(54) METHOD FOR TREATING ERECTILE DYSFUNCTION

(76) Inventor: Oleg Iliich Epshtein, Moscow (RU)

( * ) Notice: Subject to any disclaimer, the term of this patent is extended or adjusted under 35 U.S.C. 154(b) by 0 days.

(21) Appl. No.: 12/704,235

(22) Filed: Feb. 11, 2010

(65) Prior Publication Data

US 2010/0209430 A1     Aug. 19, 2010

Related U.S. Application Data

(62) Division of application No. 10/522,650, filed as application No. PCT/RU02/00368 on Aug. 2, 2002, now Pat. No. 7,700,096.

(51) Int. Cl.
*A61K 39/395*     (2006.01)

(52) U.S. Cl. .................................... 424/130.1

(58) Field of Classification Search .................. None
See application file for complete search history.

(56) References Cited

U.S. PATENT DOCUMENTS

| | | | |
|---|---|---|---|
| 3,901,967 A | 8/1975 | Cohen et al. |
| 4,963,367 A | 10/1990 | Ecanow |
| 5,683,712 A | 11/1997 | Cavazza |
| 5,741,488 A | 4/1998 | Fedlman et al. |
| 5,846,514 A | 12/1998 | Foster et al. |
| 5,879,677 A | 3/1999 | Del Zoppo |
| 5,895,783 A | 4/1999 | Garfield et al. |
| 6,150,500 A | 11/2000 | Salerno |
| 6,750,197 B1 | 6/2004 | Salerno |
| 2002/0001588 A1 | 1/2002 | Sinha |
| 2003/0099636 A1 | 5/2003 | Epshtein et al. |

FOREIGN PATENT DOCUMENTS

| | | |
|---|---|---|
| EP | 0652014 A1 | 5/1995 |
| EP | 0687466 A1 | 12/1995 |
| RU | 2007989 C1 | 2/1994 |
| RU | 2033784 C1 | 4/1995 |
| RU | 2104032 C1 | 2/1998 |
| RU | 2122858 C1 | 12/1998 |
| RU | 2137483 C1 | 9/1999 |
| RU | 2144370 C1 | 1/2000 |
| RU | 2177795 C1 | 1/2002 |
| RU | 2187334 C2 | 8/2002 |
| RU | 2192882 C1 | 11/2002 |
| WO | 9520978 A1 | 8/1995 |
| WO | 9728776 A1 | 8/1997 |
| WO | 9814161 A1 | 4/1998 |
| WO | 9814162 A1 | 4/1998 |
| WO | 9814166 A1 | 4/1998 |
| WO | 9833493 A1 | 8/1998 |
| WO | 9835680 A1 | 8/1998 |
| WO | 9921582 A2 | 5/1999 |
| WO | 0105371 A1 | 1/2001 |
| WO | 03055519 A1 | 7/2003 |

OTHER PUBLICATIONS

Borovskaya, et al., Impact of Antibodies to Endothelial No-Synthase on Sexual Behavior of Male Rats in Conditions of Seasonal Suppression of Reproductive Function, Scientific-Research Institute of pharmacology (2001) (Translation), (3 pages).
Davenas et al., Nature, 1988, 333: 816-818.
Epshtein et al. May 1999, Bulletin of Experimental Biology and Medicine,vol. 5: 493-495.
Frimel, G., ed., "Immunological Methods," Medicina Publishing House, 1987, pp. 9-33.
Goldacre (2007) Lancet 370: 1672-1673.
Grigoriev M. Yu. et al., "K probleme ispolzovaniya potentsirovannykh organnykh preparatov," Lechebno-profilakticheskaja Rabota Dlya Meditsinskikh Organizatsij V Ugolnoj Promyshlennosti, vyp. 8, 1989, izd. Tsniehi ugol (Moscow), pp. 163-165.
International Search Report from International Application No. PCT/RU02/00367, filed Aug. 2, 2002, mailed on Dec. 19, 2002.
International Search Report from International Application No. PCT/RU01/00239, filed Jun. 19, 2001, mailed on Sep. 20, 2001.
International Search Report from International Application No. PCT/RU02/00365, filed Aug. 2, 2002, mailed on Dec. 5, 2002.
International Search Report from International Application No. PCT/RU04/000374, filed Sep. 27, 2004, mailed on Feb. 10, 2005.
International Search Report from International Application No. PCT/RU02/00368, filed Aug. 2, 2002, mailed on Dec. 5, 2002.
International Search Report from International Application No. PCT/RU02/00369, filed Aug. 2, 2002, mailed on Dec. 19, 2002.
International Search Report from International Application No. PCT/RU97/00026, filed Feb. 10, 1997, mailed on Apr. 8, 1997.
Ivaniushkin, A. Ja., "Gomeopatiya i sovremennaya meditsina," Vestnik Akademii Meditsinskikh Nauk SSSR, 4, 1988, izd. "Meditsina" (Moscow), pp. 76-82.
Janeway et al. Immunobiology, 1997, 3rd edition, Garland Publishing Inc., pp. 3:1-3:11.
Jeger, J., Ed., "Clinical Immunology and Allergology" (Russian Translation), Meditsina, Moscow, 2000, pp. 358-359.
Kuznik, R.I. et al., "Cytomedines and their Role in Regulation of Physiological Functions," Uspekhi Sovremennoi Biologii, 1995, vol. 115, No. 3, pp. 353-367.
Linde et al., 1997, Lancet, vol. 350: 834-43.

(Continued)

*Primary Examiner* — Ilia Ouspenski

(74) *Attorney, Agent, or Firm* — Gilman Pergament LLP

(57) ABSTRACT

A medicament based on antibodies contains an activated form of ultra-low doses of monoclonal, polyclonal, or natural antibodies to endothelial nitric oxide synthase (NO synthase), the activated form being prepared by multiple consecutive dilutions and exposure to external factors, preferably according to the homeopathic technology. A method of treating erectile dysfunctions and vegetative disturbances of male climax by regulating the level of cyclic guanosine monophosphate (cGMP) in the cavernous bodies on sexual stimulation, the method being characterized by the use of activated forms of ultra-low doses of antibodies to the entire molecule of the endothelial NO synthase or to its polypeptide fragments, activated forms being prepared by multiple consecutive dilutions and exposure to external factors.

13 Claims, No Drawings

OTHER PUBLICATIONS

Marsden, P.A. et al., "Molecular cloning and characterization of human endothelial nitric oxide synthase," FEBS Lett., vol. 307, No. 3, pp. 287-293, 1992.

Nickeleit et al., 2007, Kid. Int. vol. 71:7-11.

Register of Pharmaceuticals of Russia, Encyclopedia of Pharmaceuticals (in Russian), Moscow, 2000, pp. 358-359.

Register of Pharmaceuticals of Russia, Encyclopedia of Pharmaceuticals (in Russian), Moscow, 2001, pp. 788-789.

Schwab, V., "Homeopathic Pharmaceutical Agents. A manual on description and preparation," Moscow, 1967, pp. 12-38.

Schwabe, W., "German Homeopathic pharmacopoeia (Homeopathisches Arzneibuch)," Stuttgart, Translation of the 5th Supplement (1991) to the 1978 edition.

Shang et al., 2005, Lancet, vol. 366: 726-32.

Stefani, D. V. et al., "Immunologiya i immunopatologiya detskogo vozrasta," Moscow, Meditsina, 1996, pp. 28, 29, 358-359.

Vasiliev, Yu, V. et al., "Gomeopatiya: vozrozhdenie traditsionnioy meditsinskoj shkoly," Vestnik Rossijkoj Akademii Nauk, 10, 1992, izd. "Nauka" (Moscow), pp. 145-148.

Vyazov, O.L., Laboratory Methods of Studies in Non-Infection Immunology (in Russian)m Moscow, Meditsina, 1968.

ered per os potentiated antibodies to NO synthase in a mix-
METHOD FOR TREATING ERECTILE DYSFUNCTION This application is a Divisional application of U.S. patent application Ser. No. 10/522,650 filed Jan. 22, 2005, which claims the benefit of International Application No. PCT/RU02/00368, filed Aug. 2, 2002, all of which are hereby incorporated herein by reference in their entireties.

FIELD OF THE INVENTION

Background of the Invention

It is a well-known practice of the treatment of pathologic syndromes by the use of antibodies (SU 1331508 A, A 61 K 39/00, 1984; SU 1730144 A1, C 12 N 7/00, 1992).

The disturbances in erection can be treated by regulation of the levels of cyclic guanosine monophosphate (cGMP) in the cavernous bodies on sexual stimulation (see Register of Pharmaceuticals in Russia, Encyclopedia of Pharmaceuticals (in Russian), Moscow, 2001, pp. 788-789). This approach enhances the relaxing effect of nitric oxide (NO) on the smooth muscles of the cavernous bodies and increases penile blood flow through the administration of a direct inhibitor of cGMP-specific phosphodiesterase Type 5. However, the duration of this effect is limited to 3-5 hours and the agent used (sildenafil citrate) is contraindicated to persons receiving nitric oxide donors or nitrates in any form.

DESCRIPTION OF THE INVENTION

The present invention is directed at obtaining an efficient medication for and a method of the treatment of erectile dysfunctions of various origin and of vegetative disorders of male climax.

The formulated objective is attained by using a medication containing an activated form of ultra-low doses of monoclonal, polyclonal or natural antibodies to endothelial nitric oxide synthase (NO synthase), the activated form being prepared by multiple consecutive dilutions and by exposure to external factors, preferably in accordance with homeopathic technology.

For preparing the antibodies one can use the entire molecule or polypeptide fragments of the enzyme (endothelial NO synthase).

The method of the treating erectile dysfunctions of various origin and of vegetative disorders of male climax through regulation of the level of cyclic guanosine monophosphate (cGMP) in the cavernous bodies on sexual stimulation involves the use of activated forms of ultra-low doses of antibodies to the entire molecule of endothelial NO synthase or to its polypeptide fragments, the activated forms being prepared by multiple consecutive dilutions and exposure to external factors.

Preferably, a mixture of various, mostly centemal, homeopathic dilutions of the antibodies indicated above should be employed.

The medication obtained in accordance with the present invention is a new pharmaceutical, which modifies the activity of NO synthase, thus intensifying the synthesis of nitric oxide in the cavernous bodies on sexual stimulation and enhancing the penile blood flow.

Unlike physiologic (therapeutic) doses of the antibodies, the activated forms of ultra-low doses of the antibodies to NO synthase do not bind (inactivate) the enzyme; instead, they modify its effects. The new medication has an effect synergic with that of NO synthase. The existence of the therapeutic effect of ultra-low doses of antibodies activated by homeopathic technology, as well as the unidirectional character of the action with the original enzyme do not follow from the state-of-the-art knowledge and have been discovered by the inventor.

EMBODIMENTS OF THE INVENTION

The new pharmaceutical is preferably prepared in the following manner.

A synthetic polypeptide corresponding to the fragment of the endothelial (Type III) NO synthase (1185-1295) with the following amino acid sequence: Glu Arg Leu His Asp Ile Glu Ser Lys Gly Leu Gln Pro Thr Pro Met Thr Leu Val Phe is obtained by solid-phase peptide synthesis (Marsden P A, Schappert K T, Chen H S, Flowers M, Sundell C L, Wilcox J N, Lamas S, Michel T Molecular Cloning and Characterization of Human Endothelial Nitric Oxide Synthase, FEBS Lett., 307:287-293, 1992).

The produced peptide, conjugated with methylated bovine serum albumin as a carrier, is used as an immunogen for immunization of rabbits. The monospecific serum to NO synthase is obtained by immunization of rabbits by this immunogen in accordance with a well-known procedure (Vyazov O. L. Laboratory Methods of Studies in Non-Infection Immunology (in Russian), Moscow, Meditsina, 1968, 356 pages). The blood is taken from an external ear vein into sterile test tubes. After the clot retraction, the serum is separated by centrifugation and heated at 56° C. for 10 min for complement inactivation.

The isolated antibodies to the endothelial NO synthase are subjected to consecutive multiple dilutions and exposed to an external mechanical impact until ultra-low or low doses are obtained, for example, according to homeopathic technology of potentization (see W. Schwabe, "Homöopathisches Arzneibuch", Stuttgart, 1978). This procedure gives rise to a uniform decrease in concentration through consecutive dilutions of 1 volumetric part of the initial matter (antibodies) in 9 volumetric parts (for decimal dilution, D) or in 99 volumetric parts (for centimal dilution, C) of a neutral solvent with multiple vertical shaking of each solution; the advantages of various containers for each subsequent dilution are used. Finally, this procedure gives the required dose (potency).

The external treatment in the course of concentration reduction can be also executed by exposure to ultrasonic, electromagnetic, or other physical factors.

The resultant medicines are used mostly in the dosage forms and dilutions adopted in the homeopathic practice: as alcoholic and aqueous solutions or as tablets (granules) prepared by impregnating the carrier contained in the dosage form by the potentised solution to saturation; also, the potentised solution can be added directly to a liquid dosage form.

Example 1

In studies of the effect of activated forms of ultra-low doses of antibodies to the endothelial NO synthase on the sexual behavior of adult male rats being under conditions of physiologic suppression of the reproductive function, we administered per os potentiated antibodies to NO synthase in a mixture of homeopathic dilutions C12+C30+C200 (within a period of 5 days, 1.5 ml per animal) to male rats 16 months old weighing 600-700 g with an established degree of sexual function suppression. After that, the male rats were placed with female rats (4 months old, weight 300 g) being in the estrous stage of the sexual cycle. Within 15 min we were registering the copulative activity on the basis of the following parameters for each male: latency of mounting (the period between the first presentation of the female and the first mounting), the number of courtships (sniffings, lickings), the total number of mountings, the number of copulations.

It was found that after 5 administrations of the preparation the number of courtships increased with high degree of significance (2 times) as against the initial indices of all animals; in 55.5% of the animals (with the initial medium and pronounced sexual activity) the indices of sexual activity increased with high degree of significance. All this testified to the stimulating effect on the sexual activity of male rats present under the conditions of physiologic suppression of the reproductive function.

Example 2

In studies of the effect of activated forms of ultra-low doses of antibodies to endothelial NO synthase on the sexual behavior of adult male rats being under conditions of seasonal suppression of the reproductive function we administered per os potentiated polyclonal antibodies to NO synthase in a mixture of homeopathic dilutions C12+C30+C200 (within a period of 5 days, 1.5 ml per animal) to male rats 4 months old weighing 400-450 g. After that, the male rats were placed with female rats (4 months old, weight 300 g) being in the estrous stage of the sexual cycle. Within 15 min we were registering the copulative activity on the basis of the following parameters for each male: the latency of mounting (the period between the first presentation of the female and the first mounting), the number of courtships (sniffings, lickings), the total number of mountings, the number of copulations.

It was found that after 5 administrations of the preparation the latency of mounting in the test group decreased with high degree of significance; at the same time, we observed an increase in the total number of mountings (2-fold) and in the number of copulations (3-fold) as against the indices obtained for the animals before administration of the drug. Thus, the administration of the preparation gave rise to the improvement of the copulative activity in male rats being under the conditions of seasonal suppression of the reproductive function, the improvement being manifested in the animals' need for repeated coitions. The accompanying decrease in the number of courtships was caused by a higher copulative activity.

Example 3

Patient S. (male), aged 51, applied to the urologist with a complaint about decreased libido, erection impairment, and lowered satisfaction from the coitus. These symptoms had been aggravating during previous two years. Over the recent 3 years the patient had been marking periodic suppressed mood, whining, memory and sleep disorders, lowered working capacity, palpitation fits, instability of the arterial blood pressure. Clinical findings: a moderate enlargement of the prostate gland. Diagnosis: erectile dysfunction against the background of involutional hormonal changes. Prescription: a mixture of homeopathic dilutions C12+C30+C200 of monoclonal antibodies to a fragment of human endothelial NO synthase, 1 tablet every 3 days. Two weeks after the beginning of treatment the patient noted better erection and an enhancement of libido against the background of the improvement of the general condition: the overall tonicity rose and the sleep became better. The recommendation was to take the preparation 1-2 times a week. On the second visit 2 months after the beginning of the treatment the patient presented no complaints; he regained libido, erection, and satisfaction from the coitus.

The invention claimed is:

1. A method of treating erectile dysfunctions by regulating the level of cyclic guanosine monophosphate (cGMP) in the cavernous bodies on sexual stimulation, said method comprising administering a homeopathically potentised form of polyclonal antibodies to endothelial NO synthase to a patient in need thereof.

2. The method according to claim 1, wherein said polyclonal antibodies are to the whole NO synthase enzyme.

3. The method according to claim 1, wherein said polyclonal, antibodies are to a fragment of the NO synthase enzyme.

4. The method according to claim 1, wherein said homeopathically potentised form comprises one or more homeopathic dilutions.

5. The method according to claim 4, wherein said one or more of the homeopathic dilutions comprises one or more centesimal homeopathic dilutions.

6. The method of treating erectile dysfunctions or vegetative disturbances of male climax by regulating the level of cyclic guanosine monophosphate (cGMP) in the cavernous bodies on sexual stimulation, said method comprising administering a homeopathically potentised form of polyclonal antibodies to a fragment of nitric oxide synthase consisting of SEQ ID NO:1, to a patient in need thereof.

7. The method of claim 6, wherein said homeopathically potentised form comprises one or more homeopathic dilution.

8. The method according to claim 7, wherein said one or more of the homeopathic dilutions comprises one or more centesimal homeopathic dilutions.

9. A method of treating vegetative disturbances of male climax by regulating the level of cyclic guanosine monophosphate (cGMP) in the cavernous bodies on sexual stimulation, said method comprising administering a homeopathically potentised form of polyclonal antibodies to endothelial NO synthase a patient in need thereof.

10. The method according to claim 9, wherein said polyclonal antibodies are to the whole NO synthase enzyme.

11. The method according to claim 9, wherein said polyclonal, antibodies are to a fragment of the NO synthase enzyme.

12. The method according to claim 9, wherein said homeopathically potentised form comprises one or more homeopathic dilutions.

13. The method according to claim 12, wherein said one or more of the homeopathic dilutions comprises one or more centesimal homeopathic dilutions.

* * * * *

SEQUENCE LISTING

```
<160> NUMBER OF SEQ ID NOS: 1

<210> SEQ ID NO 1
<211> LENGTH: 20
<212> TYPE: PRT
<213> ORGANISM: Human

<400> SEQUENCE: 1

Glu Arg Leu His Asp Ile Glu Ser Lys Gly Leu Gln Pro Thr Pro Met
1               5                   10                  15

Thr Leu Val Phe
            20
```